United States Patent [19]

Shiio et al.

[11] Patent Number: 4,618,580

[45] Date of Patent: Oct. 21, 1986

[54] PROCESS FOR THE PRODUCTION OF L-TRYPTOPHAN USING SULFAGUANIDINE-RESISTANT MICROORGANISMS

[75] Inventors: Isamu Shiio, Kamakura; Shinichi Sugimoto; Kazue Kawamura, both of Kawasaki, all of Japan

[73] Assignee: Ajinomoto Company, Incorporated, Tokyo, Japan

[21] Appl. No.: 599,922

[22] Filed: Apr. 13, 1984

[30] Foreign Application Priority Data

Apr. 13, 1983 [JP] Japan .................................... 58-65010
Dec. 23, 1983 [JP] Japan ................................. 58-243572

[51] Int. Cl.⁴ ......................... C12P 13/22; C12R 1/13; C12R 1/15
[52] U.S. Cl. .................................... 435/108; 435/840; 435/843
[58] Field of Search ................ 435/108, 253, 840, 843

[56] References Cited

U.S. PATENT DOCUMENTS 3,819,483  6/1974  Yoshinaga et al. .................. 435/107
3,849,251 11/1974  Nakayama et al. .................. 435/108

FOREIGN PATENT DOCUMENTS 2098603 11/1982 United Kingdom .

Primary Examiner—Thomas G. Wiseman
Assistant Examiner—Elizabeth C. Weimar
Attorney, Agent, or Firm—Oblon, Fisher, Spivak, McClelland & Maier

[57] ABSTRACT

A method for producing L-tryptophan by fermentation which comprises aerobically culturing in a culture medium a mutant of the genus *Corynebacterium* or genus *Brevibacterium* which is resistant to sulfaguanidine and capable of producing L-tryptophan, and recovering the L-tryptophan which has accumulated in the culture medium.

2 Claims, No Drawings

PROCESS FOR THE PRODUCTION OF L-TRYPTOPHAN USING SULFAGUANIDINE-RESISTANT MICROORGANISMS

BACKGROUND OF THE INVENTION

1. Field of the Invention

The present invention relates to a process for the production of L-tryptophan (hereinafter referred to as tryptophan) by a fermentation process.

2. Description of the Prior Art

Heretofore, there has been known, as a process for the production of tryptophan, a process which comprises producing tryptophan from a tryptophan precursor, that is, anthranilic acid, indole or 3-indolepyruvic acid. In contrast to this, the present inventors developed a process for the production of tryptophan by a direct fermentation process from a carbon source such as sugar by using a microoganism belonging to the genus Brevibacterium or the genus Corynebacterium and having resistance to tryptophan analogs such as 5-methyltryptophan, 5-fluorotryptophan etc. (Japanese Patent Publication No. 18828/1973, French Patent Application Laid-open No. 2059715, Japanese Patent Application Laid-open No. 162771/1980). It was also made clear that the amount of tryptophan accumulated is increased by imparting nutrient requirements for phenylalanine, tyrosine etc. and resistance to analogs of phenylalanine or tyrosine to these stains (Japanese Patent Publications No. 18828/1973, French Patent Application Laid-open No. 2059715) or by imparting thereto resistance to serine analogs (Japanese Patent Application Laid-open No. 174096/1982).

SUMMARY OF THE INVENTION

The present inventors have studied for the purpose of developing a process for the production of tryptophan less expensively by these direct fermentation processes and, as a result, have discovered that by imparting resistance to sulfaguanidine, known as a sulfa drug, to the heretofore known tryptophan-producing microorganisms belonging to the genus *Corynebacterium* or the genus *Brevibacterium*, tryptophan is produced in much larger amounts than by the conventional tryptophan-producing microorganisms. The present invention has been accomplished as the result of our further study based on this discovery.

DETAILED DESCRIPTION OF THE PREFERRED EMBODIMENTS

The microorganism used in the process for the production of tryptophan of the present invention is a mutant belonging to the genus *Corynebacterium* or the genus *Brevibacterium* and having the above-described properties necessary for the production of tryptophan, for example, having resistance to 5-methyltryptophan and having resistance to sulfaguanidine (it is a mutant having resistance to sulfaguanidine and capable of producing tryptophan). By employing a strain having resistances to phenylalanine analogs, tyrosine analogs, azaserine, indolemycin, decoyinine etc. and nutrient requirements for L-phenylalanine, L-tyrosine, L-histidine, L-methionine etc. in addition to the resistance to sulfaguanidine, it is possible to increase the accumulation of tryptophan.

The parent strain for the mutant of the present invention is a microorganism belonging to the genus *Corynebacterium* or the genus *Brevibacterium* known as the so-called L-glutamic acid-producing microorganism. Examples thereof include *Corynebacterium glutamicum* ATCC 13032, *Corynebacterium acetoacidophilum* ATCC 13870, *Corynebacterium lilium* ATCC 15990, *Brevibacterium flavum* ATCC 14067, *Brevibacterium divaricatum* ATCC 14020, *Brevibacterium lactofermentum* ATCC 13869, *Brevibacterium roseum* ATCC 13825.

The mutant employed in the present invention may be obtained by using the strain mentioned above as a parent strain, and subjecting it to mutating operations to impart thereto properties necessary for producing tryptophan, for example, resistance to 5-methyltryptophan and resistance to sulfaguanidine. In this case, the order of the operations for imparting these two properties is not restricted. The mutating operations may be effected in the conventional manner, for example, by irradiation with ultraviolet light or treatment with chemicals such as N-methyl-N'-nitro-N-nitrosoguanidine (hereinafter referred to as NG), nitrous acid.

Chosing *Corynebacterium glutamicum* AJ 12118 (FERM-P 7374, FERM-BP 478) and *Brevibacterium flavum* AJ 12022 (FERM-P 7034, FERM-BP 475) among the strains used in the present invention, their specific indicing methods and experimental examples showing the degrees of their resistance to sulfaguanidine are described below.

The mutants identified above by FERM-P numbers were originally deposited on Dec. 19, 1983 and Apr. 6, 1983 at the Fermentation Research Institute, Agency of Industrial Sciences and Technology, Ministry of International Trade and Industry (FRI), 1-3, Migashi 1-Chome, Yatebe-machi, Tsukuba-gun, Ibaragi-ken 305, Japan, and were accorded the FERM-P number indicated above. The mutant deposits were then converted into deposits under the Budapest Treaty on Feb. 2, 1984, and were accorded the corresponding FERM-BP numbers.

*Corynebacterium glutamicum* FERM-P 1674 was used as a parent strain. The present strain is a strain which has been exemplified in Japanese Patent Publication No. 19037/1976 (Japanese Patent Application Laid-open No. 71194/1974) and, as its properties, described as having phenylalanine and tyrosine requirements and resistance to such phenylalanine and tyrosine analogs as p-aminophenylalanine, p-chlorophenylalanine and tyrosine hydroxamate, but further possesses tryptophan analog resistance. For example, when the degree of resistance to 5-methyltryptophan which is one of the tryptophan analogs to the FERM-P 1674 strain, was compared with a natural strain of *Corynebacterium glutamicum* ATCC 13032 using the method described in French Patent Application Laid-open No. 2059715, by inoculating test media containing 600 and 900 $\mu$g/ml of 5-methyl-DL-tryptophan, respectively, with $10^6$ cells and incubating at 30° C. for 4 days, 1000 or more colonies were produced in either case with the FERM-P 1674 strain whereas there were only 122 and 0 colonies produced, respectively, with the natural strain. Thereafter, a sulfaguanidine-resistant strain was induced from the FERM-P 1674 strain. After treating with 400 $\mu$g/ml of NG at 30° C. for 15 minutes (survival rate 12%), a plate medium was prepared by adding sulfaguanidine to the synthetic medium shown in Table 1 to a concentration where the parent strain cannot grow, i.e. 1000 $\mu$g/ml.

TABLE 1

Composition of the Synthetic Medium

| Component | Concentration |
|---|---|
| Glucose | 5 g/l |
| Urea | 1.5 g/l |
| Ammonium sulfate | 1.5 g/l |
| Potassium dihydrogenphosphate | 3 g/l |
| Potassium monohydrogenphosphate | 1 g/l |
| Magnesium sulfate | 0.1 g/l |
| Calcium chloride | 0.001 g/l |
| Vitamin $B_1$ hydrochloride | 100 μg/l |
| d-Biotin | 30 μg/l |
| Minor metal elements* | 1 ml/l |
| L-Phenylalanine | 100 mg/l |
| L-Tyrosine | 100 mg/l |
| Agar | 20 g/l (pH 7.2) |

*The minor metal element solution used contains the following per liter: 8800 mg of $ZnSO_4.7H_2O$, 970 mg of $FeCl_3.6H_2O$, 270 mg of $CuSO_4.5H_2O$, 72 mg of $MnCl_2.4H_2O$, 88 mg of $Na_2B_4O_7.10H_2O$ and 37 mg of $(NH_4)_6Mo_7O_{24}.4H_2O$.

After standing at 30° C. for 10 days, the strains growing as colonies, i.e. the sulfaguanidine-resistant mutants, were harvested; of those, a mutant AJ 12118 (FERM-BP 478) excellently capable of producing tryptophan (having sulfaguanidine resistance, tryptophan analog resistance, p-aminophenylalanine resistance, p-fluorophenylalanine resistance, tyrosine hydroxamate resistance, phenylalanine requirements and tyrosine requirements). This mutant produced tryptophan in an amount 2.16 times that of the parent strain as shown in Example 1.

Thereafter, the results of the examination of the degree of resistance of this AJ 12118 strain to sulfaguanidine are shown in Table 2.

Sulfaguanidine was dissolved in the minimum medium shown in Table 1 at the concentrations shown in Table 2 to prepare plate media, which were then inoculated with about $10^7$ cells of Corynebacterium glutamicum FERM-P 1674 and Corynebacterium glutamicum AJ 12118 (FERM-BP 478), respectively, grown in a complete medium (containing 10 g/l of yeast extract, 10 g/l of polypeptone, 5 g/l of sodium chloride, 5 g/l of glucose, 200 mg/l of L-methionine and 200 mg/l of L-tyrosine and at pH 7.0), incubated at 30° C. for 3 days, and the number of colonies produced was examined. The results are shown in Table 2.

Secondly, using Brevibacterium flavum AJ 11667 (FERM-P 5907) (having 5-fluorotryptophan resistance, p-fluorophenylalanine resistance, azaserine resistance, L-tyrosine requirements and L-methionine requirements) (Japanese Patent Application Laid-open No. 174096/1982) as a parent strain, this was treated with 200 μg/ml of NG at 30° C. for 15 minutes (survival rate 11%). Then, a plate medium was prepared by adding sulfaguanidine to the synthetic medium shown in Table 3 to a concentration where the parent strain cannot grow, i.e. 1200 μg/ml, the mutation treated AJ 11667 was applied thereto and, after standing at 30° C. for 9 days, strains growing as colonies, i.e. sulfaguanidine-resistant strains were harvested; of those, a mutant AJ 12022 (FERM-BP 475) excellently capable of producing tryptophan (having sulfaguanidine resistance, 5-fluorotryptophan resistance, p-fluorophenylalanine resistance, azaserine resistance, L-tyrosine requirements and L-methionine requirements) was harvested. This mutant produced tryptophan in an amount 68% higher than the parent strain as shown in Example 2.

TABLE 3

Composition of the Synthetic Medium

| Component | Concentration |
|---|---|
| Glucose | 20 g/l |
| Ammonium sulfate | 10 g/l |
| Potassium dihydrogenphosphate | 1 g/l |
| Magnesium sulfate | 0.4 g/l |
| Ferrous sulfate | 10 mg/l |
| Manganese sulfate | 8 mg/l |
| Sodium chloride | 0.5 g/l |
| d-Biotin | 50 μg/l |
| Vitamin $B_1$.HCl | 200 μg/l |
| L-Methionine | 150 mg/l |
| L-Tyrosine | 100 mg/l |
| L-Glutamic acid | 30 mg/l |
| L-Threonine | 100 mg/l |
| Urea | 3 g/l |
| Agar | 20 g/l |
| (pH 7.2) | |

Thereafter, the results of the examination of the degree of resistance of this AJ 12022 strain to sulfaguanidine are shown in Table 2.

Sulfaguanidine was dissolved in the synthetic medium shown in Table 3 at the concentrations shown in Table 2 to prepare plate media, which were then inoculated with about $10^7$ cells of Brevibacterium flavum AJ 11667 and Brevibacterium flavum AJ 12022, respectively, grown in a complete medium (containing 10 g/l of yeast extract, 10 g/l of polypeptone, 5 g/l of sodium chloride, 5 g/l of glucose, 200 mg/l of L-methionine and 200 mg/l of L-tyrosine and at pH 7.0), incubated at 30° C. for 4 days, and the number of colonies produced was examined. The results are shown in Table 2.

As shown in Table 2, the mutants exhibited resistance to sulfaguanidine in contrast to the parent strains.

As can be seen from the experiments above, when resistance to sulfaguanidine is given to tryptophan producing microorganisms of the genus Corynebacterium or Brevibacterium by mutation, the productivity of tryptophan in the mutants obtained in remarkably increased. Mutants having resistance to sulfaguanidine also show resistance to other sulfa drugs than sulfaguanidine at the same time. Accordingly, mutants having resistance to other sulfa drugs than sulfaguanidine are sulfaguanidine resistant mutants of this invention so far as the mutants are resistant to sulfaguanidine.

TABLE 2

Degrees of Resistance of Strains to Sulfaguanidine

| | Number of Colonies Produced/Plate Medium | | | |
|---|---|---|---|---|
| | Corynebacterium glutamicum | | Brevibacterium flavum | |
| Concentration of Sulfaguanidine (μg/ml) | FERM-P 1674 | AJ 12118 (FERM-BP 478) | FERM-P 5907 | AJ 12022 (FERM-BP 475) |
| 0 | + | + | + | + |
| 1000 | − | + | | |
| 1200 | | | − | + |

(Note) In the table, (+) means that the number of colonies is 1000 or more, and (−) means that the number of colonies is zero.

In this specification, the sulfa drugs mean those sulfa drugs which have the following general features and are generally known as antagonists to p-aminobenzoic acid. They contain in their molecule a group of the general formula:

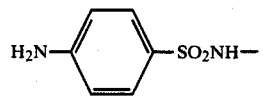

and have anti-microbial action as a general rule. The anti-microbial action against usual wild strains is suppressed by addition of p-aminobenzoic acid.

Such sulfa drugs having the foregoing features include sulfapyridine, sulfathiazole, phthalylsulfathiazole, sulfadiazine, sulfaguanidine, sulfamethazine, sulfamerazine, sulfamethoxine, sulfamethomidine, sulfamethoxyridazine, sulfisomidine, sulfaoxazole, acetosulfamine, sulfanylamide, sulfisomezole, sulfaphenazole, sulfamethizole, sulfaethidole, sulfarazine, irgafen and irgamide.

The culture medium for producing tryptophane is not particularly restricted as is a conventional medium containing a carbon source, a nitrogen source, inorganic salts, and, if necessary, organic minor nutrients. As the carbon source, carbohydrates (glucose, fructose, or hydrolysates of starch, cellulose etc., molasses etc.), organic acids (acetic acid, citric acid etc.), alcohols (glycerin, ethanol etc.) or hydrocarbons (normal paraffins etc.) may be employed. As the nitrogen source, ammonium sulfate, urea, ammonium nitrate, ammonium phosphate, ammonium chloride, ammonia gas etc. are employed, and as the inorganic salts, phosphates, magnesium salts, calcium salts, iron salts, manganese salts, and other minor metal salts are employed, according to the necessity. As the organic minor nutrients, if there are nutrient requirements, then appropriate amounts of the pertinent amino acids, vitamins, fatty acids, organic basic substances etc. are added, and, further, according to the necessity, amino acids, vitamins, AJIEKI (registered trademark; soy bean hydrolysate), yeast extract, peptone, Casamino acid, NZ amine, corn steep liquor etc. may be employed as growth promoting substances.

The incubating conditions may be conventional; for example, incubation may be conducted at pH 5-9 at a temperature of 20°-40° C. under aerobic conditions for 24-72 hours. If the pH is reduced during incubation, calcium carbonate, previously separately sterilized, is added, or neutralization is effected with alkali such as ammonia water, ammonia gas etc. On the other hand, where an organic acid is used as the carbon source, the increase in the pH is neutralized with a mineral acid or the organic acid.

Isolation and harvesting of tryptophan may be conducted in the conventional manner. It was confirmed with the obtained product that the Rf value on a paper chromatogram, the tryptophan specific reaction using Erlich reagent and the biological activity value by a microbiological quantitative method are in agreement with those of the tryptophan authentic product, and thus this was identified as tryptophan.

The quantitative assay of tryptophane was conducted according to the microbiological quantitative method using Leuconostoc mesenteroides (ATCC 8042).

The following examples are given for further understanding.

EXAMPLE 1

A medium for producing tryptophan havng the composition shown in Table 4 was allotted to 500 ml flasks, 20 ml per each, the microorganisms shown in Table 5 were inoculated in amounts of ⅓ slant respectively, and shake culture was conducted at 30° C. for 72 hours. The amount of tryptophan produced in each culture broth was as shown in Table 5.

TABLE 4

| Composition of the Medium for Producing Tryptophan | |
| --- | --- |
| Component | Concentration |
| Molasses | 100 g/l (calculated as glucose) |
| Potassium dihydrogenphosphate | 0.5 g/l |
| Potassium monohydrogenphosphate | 0.5 g/l |
| Magnesium sulfate | 0.25 g/l |
| Ammonium sulfate | 20 g/l |
| Corn steep liquor | 10 g/l |
| Calcium carbonate (separately sterilized) | 20 g/l |
| L-Phenylalanine | 200 mg/l |
| L-Tyrosine | 175 mg/l |
| (pH 7.2) | |

TABLE 5

| Amount of Tryptophan Produced | | |
| --- | --- | --- |
| Strain | Sulfaguanidine Resistance | Amount of Tryptophane Produced (g/l) |
| FERM-P 1674 | — | 4.3 |
| AJ 12118 (FERM-BP 478) | + | 9.3 |

(Note) In the table, (+) means that resistance is present, and (−) means that resistance is absent.

EXAMPLE 2

A medium for producing tryptophan having the composition shown in Table 6 was allotted to 500 ml flasks, 20 ml per each, the microorganisms shown in Table 7 were inoculated in amounts of ⅓ slant, respectively, and shake culture was conducted at 30° C. for 72 hours. The amount of tryptophan produced in each culture broth was as shown in Table 7.

TABLE 6

| Composition of the Medium for Producing Tryptophan | |
| --- | --- |
| Component | Concentration |
| Glucose | 130 g/l |
| Ammonium sulfate | 25 g/l |
| Potassium dihydrogenphosphate | 1 g/l |
| Fumaric acid | 12 g/l |
| Acetic acid | 3 ml/l |
| Manganese sulfate | 8 mg/l |
| d-Biotin | 50 μg/l |
| Vitamin $B_1$·HCl | 2000 μg/l |
| L-Tyrosine | 650 mg/l |
| DL-Methionine | 400 mg/l |
| "AJIEKI" | 50 ml/l |
| Magnesium sulfate | 1 g/l |
| Calcium carbonate (Separately sterilized) | 50 g/l |
| (pH 6.5) | |

TABLE 7

| | Amount of Tryptophan Produced | |
|---|---|---|
| Strain | Sulfaguanidine Resistance | Amount of Tryptophan Produced (g/l) |
| *Brevibacterium flavum* | | |
| AJ 11667 | — | 9.1 |
| AJ 12022 (FERM-BP 475) | + | 15.3 |

(Note) In the table, (+) means that resistance is present, and (−) means that resistance is absent.

What is claimed as new and desired to be secured by Letters Patent of the United States is:

1. A method for producing L-tryptophan by fermentation, which comprises:

culturing aerobically in a culture medium *Corynebacterium glutamicum* FERM-BP 478 or *Brevibacterium flavum* FERM-BP 475 which are resistant to sulfaguanidine and capable of producing L-tryptophan; and recovering the L-tryptophan which has accumulated in the culture medium.

2. A method for producing L-tryptophan by fermentation, which comprises:

culturing aerobically, in a culture medium containing assimilable sources of carbon and nitrogen and inorganic salts, *Corynebacterium glutamicum* FERM-BP 478 or *Brevibacterium flavum* FERM-BP 475, or mutants thereof, which are resistant to sulfaguanidine and capable of producing L-tryptophan; and recovering the L-tryptophan accumulated in said culture medium.

* * * * *